(12) United States Patent
Rudolph

(10) Patent No.: US 11,956,209 B2
(45) Date of Patent: Apr. 9, 2024

(54) HIPAA COMPLIANT DISTRIBUTED DATA

(71) Applicant: Volker Rudolph, Munich (DE)

(72) Inventor: Volker Rudolph, Munich (DE)

(*) Notice: Subject to any disclaimer, the term of this patent is extended or adjusted under 35 U.S.C. 154(b) by 381 days.

(21) Appl. No.: 17/495,205

(22) Filed: Oct. 6, 2021

(65) Prior Publication Data

US 2022/0116357 A1    Apr. 14, 2022

Related U.S. Application Data

(60) Provisional application No. 63/089,494, filed on Oct. 8, 2020.

(51) Int. Cl.
*H04L 9/40* (2022.01)
*G16H 10/65* (2018.01)

(52) U.S. Cl.
CPC ......... *H04L 63/0218* (2013.01); *G16H 10/65* (2018.01); *H04L 63/1416* (2013.01); *H04L 63/168* (2013.01)

(58) Field of Classification Search
CPC ............. H04L 63/0218; H04L 63/1416; H04L 63/168; G06H 10/65
USPC ............................................. 726/11
See application file for complete search history.

(56) References Cited

U.S. PATENT DOCUMENTS

| | | |
|---|---|---|
| 9,202,084 B2 | 12/2015 | Moore |
| 10,482,398 B2 | 11/2019 | Hammad |
| 2016/0275637 A1 | 9/2016 | Grant et al. |
| 2017/0187748 A1* | 6/2017 | Durand ............... H04L 63/1475 |
| 2020/0082922 A1* | 3/2020 | Bacastow ............. G16H 10/60 |
| 2021/0158921 A1* | 5/2021 | Panchal ................. H04N 23/50 |

* cited by examiner

*Primary Examiner* — Michael S McNally
(74) *Attorney, Agent, or Firm* — A, T, & P pc; Pete Tormey

(57) ABSTRACT

Disclosed herein are systems and methods for storing patient medical information on a local processing device, anonymizing a portion of that medical information and storing it on a second processing device, exposing that anonymized medical information to a third processing device coupled to the second processing device through a network, and restricting users of the third processing device to only accessing HIPAA compliant medical information. Alarms are included for indicating the improper transfer of HIPAA data.

14 Claims, 3 Drawing Sheets

HIPAA COMPLIANT DISTRIBUTED DATA

PRIORITY

This application claims the benefit of patent application Ser. No. 63089494 filed Oct. 8, 2020, by the same inventor, which, together with its appendix, is included by reference as if fully set forth herein.

BACKGROUND

A problem with structured data storage is the ability to maintain confidentiality when and if the data store is hacked or compromised. This is most readily apparent for the storage of medical information, where the Health Insurance Portability and Accountability Act (HIPPA) provides for a very high degree of privacy even within a single institution.

For operations like securing vaccination trial records, large record sets of medical research data needs to be scrubbed of personal identification information (PII) before it can be shared to protect a person's medical history and treatment.

Presented herein are systems and methods for addressing these well-known deficiencies in data management of personal identifiable information.

SUMMARY

Disclosed herein are systems and methods for storing patient medical information on a local processing device, anonymizing a portion of that medical information and storing it on a second processing device, exposing that anonymized medical information to a third processing device coupled to the second processing device through a network, and restricting users of the third processing device to only accessing HIPAA compliant medical information. Alarms are included for indicating the improper transfer of HIPAA data.

Some embodiments may be system for securing data including a user interface operable to receive medical information including a patient and a patient medical data with personally identifiable information (PII) and store it in a first structured data store having local index. A second structured data store may be included operable to receive some of the medical data, including anonymized medical data, and a second index that is different from the local index, so the local index and the second index are configured to only allow for one-way indexing.

The system may also include a multi-layered firewall separating the first structured data store and the second structured data store. The multi-level firewall securing the local structured data store in a first zone and the second structured data store in a second zone. An alarm engine alerts when PII has crossed from a first zone to the second zone.

The construction and method of operation of the invention, however, together with additional objectives and advantages thereof will be best understood from the following description of specific embodiments when read in connection with the accompanying drawings.

DESCRIPTION

Generality of Invention

Figure 1:
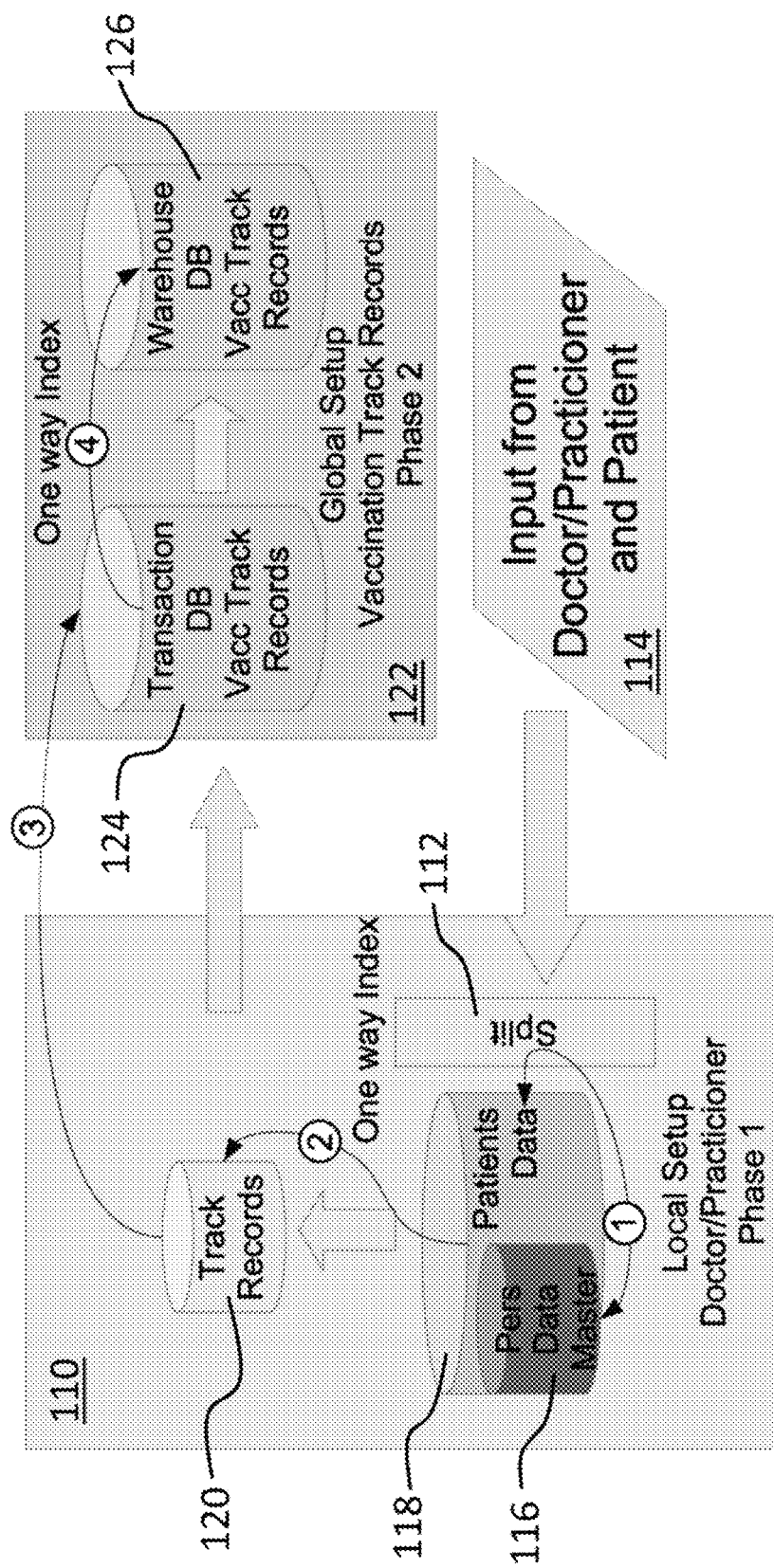
FIG. 1 shows a block diagram of an embodiments which may be used according to the present disclosure.

This application should be read in the most general possible form. This includes, without limitation, the following:

References to specific techniques include alternative and more general techniques, especially when discussing aspects of the invention, or how the invention might be made or used.

References to "preferred" techniques generally mean that the inventor contemplates using those techniques, and thinks they are best for the intended application. This does not exclude other techniques for the invention, and does not mean that those techniques are necessarily essential or would be preferred in all circumstances.

References to contemplated causes and effects for some implementations do not preclude other causes or effects that might occur in other implementations.

References to reasons for using particular techniques do not preclude other reasons or techniques, even if completely contrary, where circumstances would indicate that the stated reasons or techniques are not as applicable.

Furthermore, the invention is in no way limited to the specifics of any particular embodiments and examples disclosed herein. Many other variations are possible which remain within the content, scope and spirit of the invention, and these variations would become clear to those skilled in the art after perusal of this application.

Lexicography

The terms "effect", "with the effect of" (and similar terms and phrases) generally indicate any consequence, whether assured, probable, or merely possible, of a stated arrangement, cause, method, or technique, without any implication that an effect or a connection between cause and effect are intentional or purposive.

The terms "Extrusion detection" or "outbound intrusion detection" generally refers to tools and techniques to identify successful and unsuccessful attempts to use the resources of a computer system to compromise other systems. Extrusion detection techniques may focus primarily on the analysis of system activity and outbound traffic to detect malicious users, malware or network traffic that may pose a threat to the security of neighboring systems. Extrusion detection systems try to prevent attacks from being launched in the first place. They may implement monitoring controls at leaf nodes of the network—rather than concentrating them at choke points, e.g., routers—in order to distribute the inspection workload and to take advantage of the visibility a system has of its own state. The goal of extrusion detection is to identify attack attempts launched from an already compromised system to prevent them from reaching their target, hereby containing the impact of the threat.

The term "relatively" (and similar terms and phrases) generally indicates any relationship in which a comparison is possible, including without limitation "relatively less", "relatively more", and the like. In the context of the invention, where a measure or value is indicated to have a relationship "relatively", that relationship need not be precise, need not be well-defined, need not be by comparison with any particular or specific other measure or value. For example and without limitation, in cases in which a measure or value is "relatively increased" or "relatively more", that comparison need not be with respect to any known measure or value, but might be with respect to a measure or value held by that measurement or value at another place or time.

The term "substantially" (and similar terms and phrases) generally indicates any case or circumstance in which a determination, measure, value, or otherwise, is equal, equivalent, nearly equal, nearly equivalent, or approximately, what the measure or value is recited. The terms "substantially all" and "substantially none" (and similar terms and phrases) generally indicate any case or circumstance in which all but a relatively minor amount or number (for "substantially all") or none but a relatively minor amount or number (for "substantially none") have the stated property. The terms "substantial effect" (and similar terms and phrases) generally indicate any case or circumstance in which an effect might be detected or determined.

The terms "this application", "this description" (and similar terms and phrases) generally indicate any material shown or suggested by any portions of this application, individually or collectively, and include all reasonable conclusions that might be drawn by those skilled in the art when this application is reviewed, even if those conclusions would not have been apparent at the time this application is originally filed.

Detailed Description

Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Processing System

The methods and techniques described herein may be performed on coupled processor-based devices. These processor-based devices will generally comprise a processor attached to one or more memory devices or other tools for persisting data. These memory devices will be operable to provide machine-readable instructions to the processors and to store data. Certain embodiments may include data acquired from remote servers. The processor may also be coupled to various input/output (I/O) devices for receiving input from a user or another system and for providing an output to a user or another system. These I/O devices may include human interaction devices such as keyboards, touch screens, displays and terminals as well as remote connected computer systems, modems, radio transmitters and handheld personal communication devices such as cellular phones, "smart phones", digital assistants and the like.

The processing system may also include mass storage devices such as disk drives and flash memory modules as well as connections through I/O devices to servers or remote processors containing additional storage devices and peripherals.

Certain embodiments may employ multiple servers and data storage devices thus allowing for operation in a cloud or for operations drawing from multiple data sources. The inventor contemplates that the methods disclosed herein will also operate over a network such as the Internet, and may be effectuated using combinations of several processing devices, memories and I/O. Moreover, any device or system that operates to effectuate techniques according to the current disclosure may be considered a server for the purposes of this disclosure if the device or system operates to communicate all or a portion of the operations to another device.

The processing system may be a wireless device such as a smart phone, personal digital assistant (PDA), laptop, notebook and tablet computing devices operating through wireless networks. These wireless devices may include a processor, memory coupled to the processor, displays, keypads, WiFi, Bluetooth, GPS and other I/O functionality. Alternatively, the entire processing system may be self-contained on a single device.

To effectuate operations, processor-readable instructions may be encoded in memory to direct the processor to perform certain functions. These functions may also be encapsulated into software "engines" which are generally dedicated functions for performing specific tasks. Collections of engines may be employed in certain embodiments to effectuate the methods disclosed herein.

A client-server system may rely on "engines" each of which may be responsible for differing operations and may reside in whole or in part on a client, server or other device. As disclosed herein a reporting engine, a data engine, an execution engine, a user interface (UI) engine and the like may be employed. These engines may seek and gather information about events from remote data sources. Besides engines for querying and reporting on data, certain embodiments may also include a parser engine for manipulating data.

Localized means a processor system setup which is completely managed by the individual user. It may be the personal mobile device, an intranet installation or a cloud-based installation meant to be used exclusively by the individual or institution.

One-way indexing data generally means that an upload operation of information will work by resolving the next index from an inner layer to an outer layer. A reverse transaction is prohibited. because the information is missing to resolve the backward indexing. If the personal records of the patient are lost (together with the first index) on the local installation, the patients records cannot be updated towards the warehouse database because the reference to the track records is lost.

An extrusion detection firewall supports the process of anonymization. The conventional intrusion detection firewall works in the opposite direction of an extrusion detection firewall. The intrusion detection firewall is protecting data from attacks from outside; an extrusion detection firewall protects from being taken to the outer world, i.e. the public. Firewall reports are registering attacks on the network layer, whereas HIPAA reports are detecting breaches on the application layer. The extrusion detection firewall is generating the HIPAA reports.

Embodiments

FIG. 1 shows a block diagram of an embodiments which may be used according to the present disclosure. In FIG. 1 input 114 from a user such as a doctor, patent, or other medical practitioner is entered into a local processing device 110 using a user interface. The local processing device include a parsing engine 112 which is operative to remove personally identifiable information (PII) from the input 114. Once parsed the input 114 is stored in two separated data structures, a personal data master 116 and a patient data structure 118. Collectively the personal data master 116 and the patients data structure 118 (the Master Data structure) are indexed to a medical track record 120 such as a vaccination record as shown. The track records 120 reside on the local processor 110. The track records 120 may not be related to the patient's personal data because indexing is one way, thus requiring knowledge of the Master Data Table (kept secure on local site) to resolve the patient's personal identification data.

A remote processing system 122 includes a transaction database 124 related to the Track Records 120, and a Warehouse database 126. A global engine (not shown) disposed to operate on the remote processing system 122 controls operations for control of data on the remote processing system 122. This control of data provides for the transaction database 124 to receive track record information 120 from the local processing system 110. Access to the data is secured, in part, through conventional firewall techniques.

Figure 2:
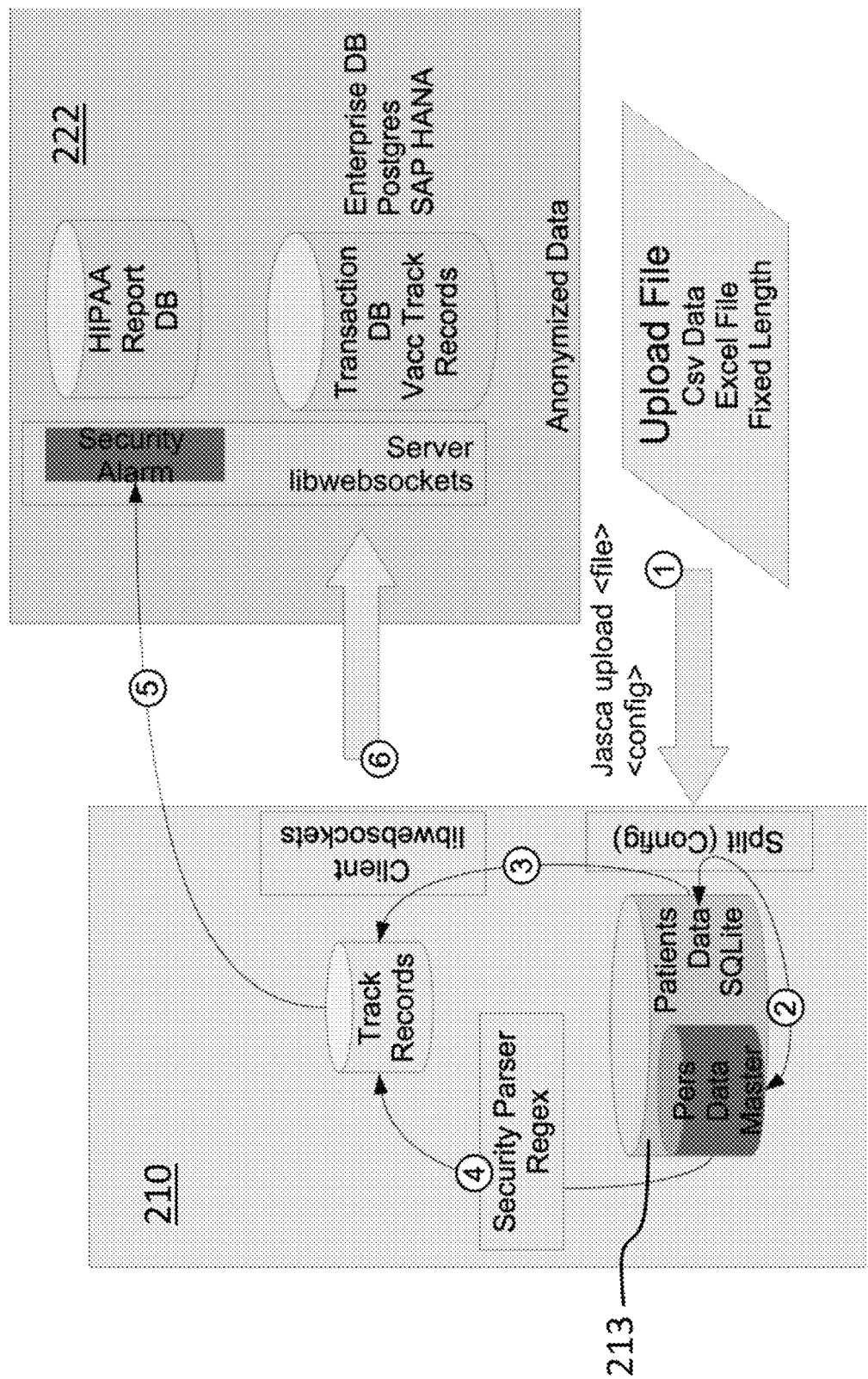
FIG. 2 shows a diagram illustrating embodiments of certain operations according to the current disclosure.

FIG. 2 shows a diagram illustrating embodiments of certain operations according to the current disclosure. At a process 1 a user, such as a medical professional or patient uploads their medical information into the local processing system 210. Software engines programmatically split the medical information to separate PII from payload medical data and store it in a master data structure 213. The master data structure 213 isolates the PII from the remaining medical information.

At a process 3 medical track records are prepared for exposure to a network using a libwebsocket client application. At a process 4, the track records are parsed with input from the master data structure 213 to create anonymized track records. Conventional techniques may be employed to anonymize the track records such as data masking, pseudonymization, generalization, data swapping, and the like.

At a process 5 a HIPAA alarm engine is employed on a network processing system 222 using an application operable to control data flow and report errors. The HIPAA security alarm operates to detect malfunctioning anonymization which may occur during configuration. through user error, or other processes.

At a process 6 anonymized track record are exposed to a network through a libwebsocket Client. The libwebsocket Client is coupled over the network to a corresponding libwebsocket server on a remote processing system 222 for the transfer of anonymized data. The remote processing system may store HIPAA report data and an anonymized Track records. The data on remote processing system 222 may be accessible to users for providing reporting information about medical information. For example, and without limitation vaccination records.

References in the specification to "one embodiment", "an embodiment", "an example embodiment", etc., indicate that the embodiment described may include a particular feature, structure or characteristic, but every embodiment may not necessarily include the particular feature, structure or characteristic. Moreover, such phrases are not necessarily referring to the same embodiment. Further, when a particular feature, structure or characteristic is described in connection with an embodiment, it is submitted that it is within the knowledge of one of ordinary skill in the art to effect such feature, structure or characteristic in connection with other embodiments whether or not explicitly described. Parts of the description are presented using terminology commonly employed by those of ordinary skill in the art to convey the substance of their work to others of ordinary skill in the art.

Indexing

Multiple layers of indexing may be employed to protect bundled data such as anonymized patient records. This one-way index may be effectuated first using localized and correct indexed data (Patients personal information to medical data) to an abstract index, then yet an anonymized index, which doesn't have any way to resolve to the personal data (doctor, patient, vaccination producer or else) of the first localized index. The resolution of the anonymized index may only be to bundle the anonymized medical data (vaccine production, vaccine transport, medical investigation, etc.) of a patient as an unknown person. Additionally, in some embodiments, each database may only index "downstream" such that an intruder in a downstream database cannot reach "upstream" into data localized on the medical practitioner's premises.

Accordingly, any new index will block the way towards the personal data, which is only locally available on the computer of the medical practitioner. If the local database is somehow exposed to the public (say by a firewall issue on the intranet, personal copying the data, etc.) only a very small portion of the warehouse DB will be exposed with HIPAA identifiers found. It will be difficult to find the associated records on the warehouse DB. Therefore, only the local installation is exposed—not the warehouse data. If the transaction DB is exposed from an unauthorized access, the intruder only can tell which medical practitioner has a number of patients, but it will be difficult to match patient data to the index on the medical practitioner's localized site.

Operating in conjunction with the transaction database 124 is the warehouse database 126. From the transaction database 124 a user may generate HIPAA reports by parsing the medical information. Conventional intrusion detection for firewalls may be implemented as well. Certain embodiments may be set up to block the access to data which can be related to the doctor or patient. The transaction database 124 holds the higher level (third) index, which may be resolved to the application's registration or the medical practitioner's location. Once resolved the application may record the HIPAA record.

An example of indexing may include a pair of indexes 3 and 4. If the 3rd index is a composition of the 2nd index on the track records on a local site and the registration index (the 4th index) is completely newly generated. Then the relation between the 3rd Index and the 4th index is kept inside the transaction Database. Examples of indices may include:

2nd Index: Unique Index (and unrelated to the personal information) on the local Database regarding Track Records. Example: 100200300, this unique index is mapped towards a newly created index, 999 (the 999 patient, who is vaccinated and data is taken). If it is moved to the global transaction database the Index may again be changed (randomized).

$3^{rd}$ Index: Composition of Registration Index App, Example: jascaReg5000 (an application index) and $2^{nd}$ Index 999 yields JascaReg500_999. This index may also be randomized and uncorrelated.

$4^{th}$ Index: newly generated Index for an anonymized 999999 (the number of the anonymized patient, who entered the warehouse DB as the 1 millionth person less 1).

Using these representative indices, one cannot resolve the index 999999 to JascaReg500_100200300 from just the warehouse DB. Similarly, from the transaction database index you cannot resolve to the local database index JascaReg500_random(999) or deeper to 100200300. Each mapping is kept local. The transaction database has the mapping for the warehouse database records. The local database has the mapping for the track records.

If a user finds in the transaction database a personal record, say for example a Mr. Scott has come to a medical office, the extrusion detection firewall will raise an automated HIPAA alarm indicating disclosure of PII. The Firewall will block the record from being transmitted to the warehouse database. The HIPAA information is related towards the Index JascaReg500_999 and the index 999 cannot be resolved towards the local personal database.

Moreover, the registration index jascaReg500 can tell which medical practitioner was attempting to transmit one of the HIPAA Identifiers.

An extrusion detection firewall may be applied on the local site as well. Note: On local site there may be 18 HIPAA identifiers in the local personal data, accordingly the extrusion detection firewall will explicitly search for these identifiers in the track records. If there is a match with one or more of the HIPAA identifiers an alarm is raised, and the track record access will be blocked.

Figure 3:
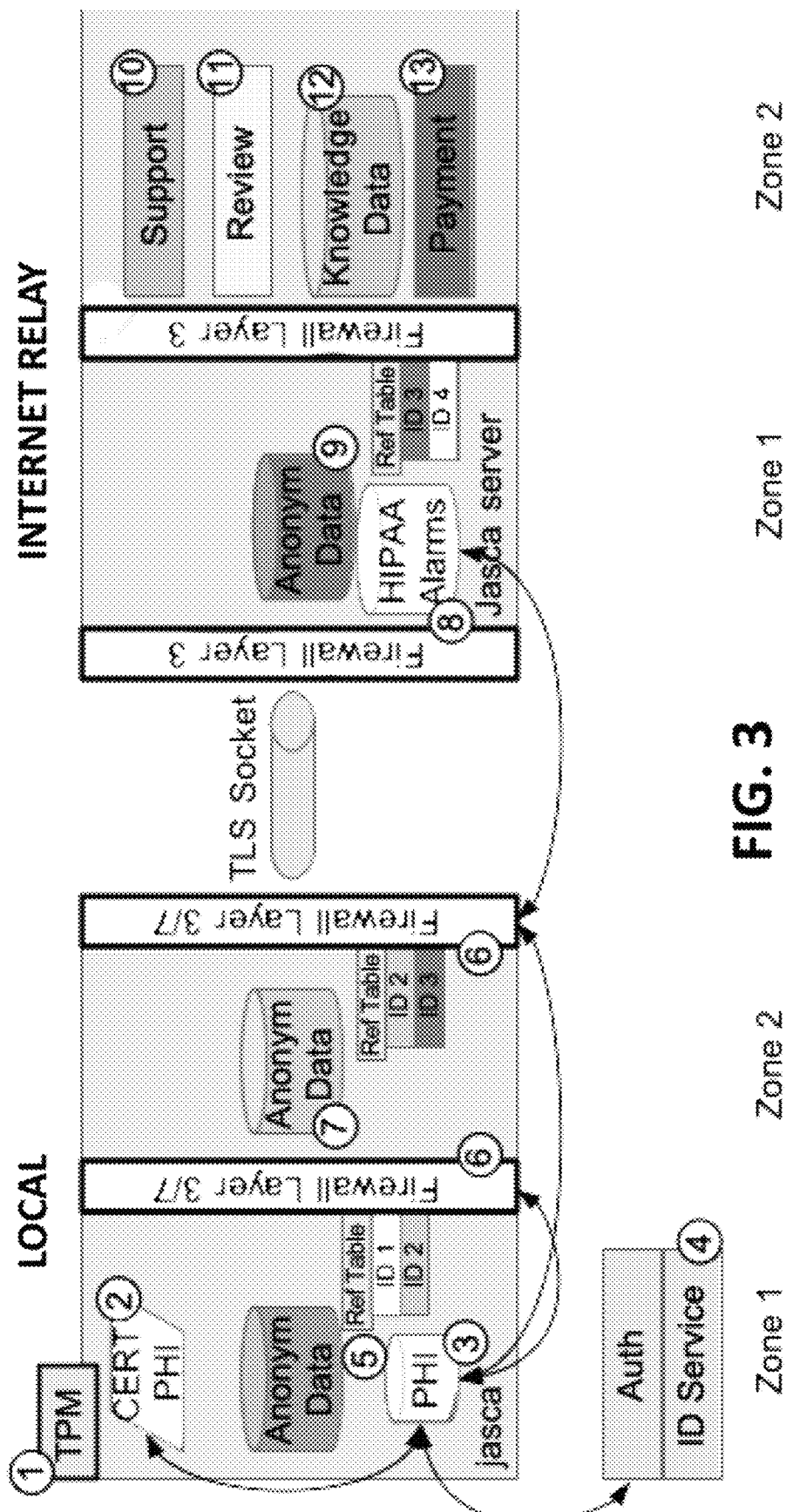
FIG. 3 shows another embodiment of a system using the techniques disclosed herein.

FIG. 3 shows another embodiment of a system using some of the techniques disclosed herein. TPM 1 is a public key infrastructure (PKI) System for device identification and secure keystore such as trusted platform module (TPM) and hardware security module (HSM). While this description shows functional block diagrams, embodiments may be effectuated using dedicated hardware for certain operations. For example, and without limitation, a secure server may be located at a user's facility. This secure server may perform some operations as disclosed herein. The local device may be built on common, easily-to-obtain devices such as a RASBERRY PI processor.

A personal health information (PHI) certificate 2 may employ a X509 certificate using X509 extensions. The X.509 certificates bind an identity to a public key using a digital signature. In an X.509 system, there are two types of certificates. The first is a CA certificate. The second is an end-entity certificate. A CA certificate can issue other certificates. The extensions employed may be protected health information (PHI) parameters.

PHI database table 3 provides information related to the PHI parameter certificate. The PHI database 3 may be coupled to a user, such as a medical provider or doctor's office.

Identity provider 4 combines device identification with an external identity provider for health professionals. This provides for a medical professional to authenticate, via an external identity provider (such as gematik IDP), using his health professional ID card (HBA). Third-party identifiers certify the identity of a user who has been authenticated to him as well as various attributes required for this such as an HBA card.

A split-zone data structure having one portion in zone 1 and the other in zone 2 (5 and 7 respectively) may be used to provide for enhanced security. The zones are separated by firewall 6. The database is normalized against PHI parameters and therefore split into at least 2 data tables, one containing the PHI parameters. and one table containing the health data. Both tables are joined using a database indexing scheme such as those described herein.

The application firewalls are configured with reference to the PHI Parameters (i.e cert, table) to scan the content being transmitted from zone 1 to zone 2. In this representative example, zone 1 incudes secure data that is not anonymized whereas zone 2 includes only anonymized data. During transit, anonymized HIPAA Alarms may be sent in response to the scanning. The HIPAA security alarm operates to detect malfunctioning anonymization which may occur during configuration, through user error, or other processes. Malfunctioning is broadly defined to include the improper transmission of personally identifiable information (PII). A HIPAA alarm database 8 may store information regarding HIPAA violations and HIPAA alarms for further use. These uses may include building "smarter" alarms using neural networks and other artificial intelligence techniques.

Zone 2 provides for the anonymization of health information. Anonymization may be effectuated using conventional techniques such as those disclosed herein or otherwise available.

Zone 1 and zone 2 may be separated by multiple level firewalls using both open systems interconnection (OSI) layer 3 and layer 7 protocols. Where most firewall protocol only inspect headers at layer 3 (IP address), 4 (Transport), and 5 (Port), a layer 7 protocol inspects the payload of packets to match against known traffic types. Layer 3 Firewalls (Network Firewalls) often categorize traffic according to IP addresses, port numbers and service protocols. This is also sometimes known as the network layer. Layer 7, the application layer of the OSI (Open System Interconnection) Model, supports application and end-user processes, such as HTTP and SMTP. Many application-layer firewalls allow for filters to intercept, analyze or modify traffic specific to your network conditions.

Internet Relay

An Internet relay may provide an interface for access to anonymized data through a network. The Internet relay may be effectuated as an engine providing multiple user interfaces and performing multiple operations to provide HIPAA compliant data. These interfaces may include one or more of:

Support 10 for maintaining control of the system and allowing access to users;
Review 11 for validating the data and usage;
Knowledge data 12, for storing information gleaned from usage and for providing raw material for artificial intelligent operations, and
Payment 13 to automate billing and monetization.

The Internet Relay also provides operations to verify the quality and reliability of the anonymized data 9 and HIPAA alarms 8. While the Internet Relay shown includes connections to interfaces, this application should not be read as limiting in anyway. For example, the Internet Relay could operate through messaging, email or other network channels.

System Initialization

Certain embodiments may include method steps as detail here to initialize a system. This process may be performed in a medical professional's office.

1. A smart card reader takes the information from an eHealth Subscriber Identity Module (SIM) card, which may include the commonly known PHI Parameters. An eHealth SIM card would be issued to a verified user assuring a degree of security.

2. A certificate is generated to guarantee access to a system wherein the certificate contains the PHI parameters in the extensions as described herein.

3. The certificate is used to control Anonymization. The eHealth subscriber identity module (SIM) does not contain all of the parameters, only a portion. Additional PHI parameters may be added in certain embodiments.

The uniqueness of this process is granting access on the one hand by using the eHealth SIM and then configuring a firewall at the application layer, which controls the anonymization.

Communications Channel

Certain embodiments may include one or more communications (chat) channels allowing users to communication with respect to the medical data. For example, and without limitation, a patient may communicate with a medical professional exchange text, reports, pictures and other data with a doctor. When a database session, such as an SQL Session, is created a data access object that represents a communication channel between the application and the database management system (DBMS) is created. An application can have several sessions opened at once, thus allowing more than one transaction active at the same time. Also, the same SQL session can be shared by different data sources. Conventionally, these sessions may include a chat channel such as those employed by SQLPLUS. This chat operation allows for users to interact using similar security as the DBMS.

Some operations of the communications channel may include:
- The vaccinee (patient) can get reports from the warehouse database (anonymized), but not write data to a global setup file.
- The vaccinee may send reports to a doctor and start chatting about these reports
- The chat may be under control of the medical practitioner and only information approved by the doctor may be published in the vaccination track record.

The above illustration provides many different embodiments or embodiments for implementing different features of the invention. Specific embodiments of components and processes are described to help clarify the invention. These are, of course, merely embodiments and are not intended to limit the invention from that described in the claims.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the invention, as set forth in the following claims.

What is claimed:

1. A system for securing data including:
   a user interface, said user interface operable to receive medical information including a patient and a patient medical data including a personally identifiable information (PII) and store it in a first structured data store, said first structured data store including a local index;
   a second structured data store operable to receive a portion of the medical data, said second structured data store including anonymized medical data, and a second index different from the local index;
   wherein the local index and the second index are configured to only allow for one-way indexing;
   a multi-layered firewall separating the first structured data store and the second structured data store, said multi-level firewall securing the local structured data store in a first zone and the second structured data store in a second zone, and
   an alarm engine, said alarm engine operable to alert when PII has crossed from a first zone to the second zone.

2. The system of claim 1 further including:
   a subscriber identity module (SIM) and a SIM reader, said SIM encoded with medical information from a verified source,
   wherein the SIM reader is operable to transfer medical information on the SIM to the first structured data store.

3. The system of claim 1 wherein the multi-level firewall includes security at the open systems interconnection (OSI) application layer and the OSI network layer.

4. The system of claim 1 wherein the alarm engine monitors network traffic for known PII.

5. The system of claim 1 wherein the local index and the second index are related to each other through a third structured data store.

6. A method for providing secure data including:
   receiving medical information at a server, said server coupled to a network, said medical information including a patient and a patient medical data including a personally identifiable information (PII);
   storing the medical information in a first structured data store, said first structured data store including a local index;
   anonymizing the medical information and storing it in a second structured data store, said second structured data store including a second index different from the local index, wherein the local index and the second index and configured to only allow for one-way indexing;
   separating the first structured data store and the second structured data store with a multi-layered firewall, said multi-level firewall securing the local structured data store in a first zone and the second structured data store in a second zone, and
   indicating an alarm when PII has crossed from a first zone to the second zone.

7. The method of claim 6 further including:
   reading a subscriber identity module encoded with medical information from a verified source,
   wherein the medical information on the SIM is transferred to the first structured data store.

8. The method of claim 6 wherein the multi-level firewall includes security at the open systems interconnection (OSI) application layer and the OSI network layer.

9. The method of claim 6 wherein the alarm engine monitors network traffic for known PII.

10. One or more machine-readable storage devices encoded with non-transitory instructions directing a processor to perform a method including:
    receiving medical information, said medical information including a patient and a patient medical data including a personally identifiable information (PII);
    storing the medical information in a first structured data store, said first structured data store including a local index;
    anonymizing the medical information and storing it in a second structured data store, said second structured data store including a second index different from the local index, wherein the local index and the second index and configured to only allow for one-way indexing;
    separating the first structured data store and the second structured data store with a multi-layered firewall, said multi-level firewall securing the local structured data store in a first zone and the second structured data store in a second zone, and
    indicating an alarm when PII has crossed from a first zone to the second zone.

11. The method of claim 10 further including:
    reading a subscriber identity module encoded with medical information from a verified source,
    wherein the medical information on the SIM is transferred to the first structured data store.

12. The method of claim 10 wherein the multi-level firewall includes security at the open systems interconnection (OSI) application layer and the OSI network layer.

13. The method of claim 10 wherein the alarm engine monitors network traffic for known PII.

14. The method of claim 10 further including:
relating the local index to the second index through a third structured data store.

\* \* \* \* \*